United States Patent
Mai

(10) Patent No.: US 9,568,404 B2
(45) Date of Patent: Feb. 14, 2017

(54) METHOD AND APPARATUS FOR BIOMOLECULE ANALYSIS

(71) Applicant: Junyu Mai, Walnut Creek, CA (US)

(72) Inventor: Junyu Mai, Walnut Creek, CA (US)

( * ) Notice: Subject to any disclaimer, the term of this patent is extended or adjusted under 35 U.S.C. 154(b) by 0 days.

(21) Appl. No.: 14/662,117

(22) Filed: Mar. 18, 2015

(65) Prior Publication Data
US 2015/0330879 A1    Nov. 19, 2015

Related U.S. Application Data

(60) Provisional application No. 61/994,645, filed on May 16, 2014.

(51) Int. Cl.
*B01D 35/00* (2006.01)
*G01N 1/40* (2006.01)
(Continued)

(52) U.S. Cl.
CPC .......... *G01N 1/4077* (2013.01); *G01N 33/525* (2013.01); *G01N 33/542* (2013.01);
(Continued)

(58) Field of Classification Search
CPC .. G01N 1/4077; G01N 33/525; G01N 33/542; G01N 33/54386; G01N 33/54393; G01N 2001/408; C12Q 1/04
(Continued)

(56) References Cited

U.S. PATENT DOCUMENTS

| | | | |
|---|---|---|---|
| 4,230,685 | A | 10/1980 | Senyei et al. |
| 4,366,241 | A | 12/1982 | Tom et al. |

(Continued)

FOREIGN PATENT DOCUMENTS

| | | |
|---|---|---|
| CA | 1288690 C | 9/1991 |
| EP | 0106536 A2 | 4/1984 |

(Continued)

OTHER PUBLICATIONS

Bagramyan, et al. "9. Attomolar Detection of Botulinum Toxin Type A in Complex Biological Matrices" PloS ONE 3(4): e2041, 1-9, 2008.
(Continued)

*Primary Examiner* — Dennis M White
(74) *Attorney, Agent, or Firm* — Zhe Wu

(57) ABSTRACT

Disclosed are devices or apparatus and methods for membrane-, bead- or cell-based biomolecule analysis, where a detectable signal can be measured after affinity binding and/or enzymatic reaction occurs on the membranes, beads or cells. The apparatus or device can rapidly separate the beads or cells from the liquid solution without using centrifugation, vacuum, or magnetic force. The apparatus or device includes a sample well for receiving a sample containing cells or beads, as well as other aqueous solutions, a porous filter membrane at the bottom of the well which is capable of retaining the cells or beads on its upper surface by size exclusion, and an absorbing plug in touch with the filter membrane for removing the liquid solution. Multiple devices can be arranged in a multi-well array in a plate so that signals from multiple assays can be directly analyzed in a plate reader or an imaging instrument.

28 Claims, 20 Drawing Sheets

(51) Int. Cl.
*G01N 33/543* (2006.01)
*G01N 33/542* (2006.01)
*G01N 33/52* (2006.01)

(52) U.S. Cl.
CPC . *G01N 33/54386* (2013.01); *G01N 33/54393* (2013.01); *G01N 2001/4088* (2013.01)

(58) Field of Classification Search
USPC .......................................................... 422/535
See application file for complete search history.

(56) References Cited

U.S. PATENT DOCUMENTS

| | | | |
|---|---|---|---|
| 4,486,315 A | 12/1984 | Teipel | |
| 4,632,901 A | 12/1986 | Valkirs et al. | |
| 4,734,192 A | 3/1988 | Champion et al. | |
| 4,797,259 A | 1/1989 | Matkovich et al. | |
| 4,818,677 A | 4/1989 | Hay-Kaufman et al. | |
| 4,853,335 A | 8/1989 | Olsen et al. | |
| 4,857,453 A | 8/1989 | Ullman et al. | |
| 4,897,193 A | 1/1990 | Cais et al. | |
| 4,902,481 A | 2/1990 | Clark et al. | |
| 4,912,034 A | 3/1990 | Kalra et al. | |
| 5,120,504 A | 6/1992 | Petro-Roy et al. | |
| 5,185,127 A * | 2/1993 | Vonk | B01L 3/5023 422/408 |
| 5,380,437 A | 1/1995 | Bertoncini et al. | |
| 5,424,725 A * | 6/1995 | Wandt | H01M 2/1055 340/7.63 |
| 5,425,725 A | 6/1995 | Tanzer et al. | |
| 5,620,663 A | 4/1997 | Aysta et al. | |
| 5,879,881 A | 3/1999 | Rubenstein et al. | |
| 5,989,924 A | 11/1999 | Root et al. | |
| 6,169,394 B1 | 1/2001 | Frazier et al. | |
| 6,309,605 B1 | 10/2001 | Zermani et al. | |
| 6,489,132 B1 | 12/2002 | Gordon et al. | |
| 6,558,959 B2 | 5/2003 | Chu | |
| 7,063,216 B2 | 6/2006 | Lane et al. | |
| 7,211,224 B2 * | 5/2007 | Olivier | B01L 3/50255 206/569 |
| 8,182,766 B2 | 5/2012 | Olivier et al. | |
| 2001/0048893 A1 | 12/2001 | Norris et al. | |
| 2002/0098125 A1 | 7/2002 | Roberts et al. | |
| 2003/0000884 A1 | 1/2003 | Hamlin et al. | |
| 2003/0173287 A1 | 9/2003 | Johnston et al. | |
| 2004/0081979 A1 * | 4/2004 | Knezevic | B01L 3/5023 435/6.14 |
| 2005/0221403 A1 * | 10/2005 | Gazenko | C12Q 1/04 435/7.32 |
| 2006/0138052 A1 | 6/2006 | Leistner et al. | |
| 2007/0042499 A1 | 2/2007 | Schwind et al. | |
| 2007/0187249 A1 | 8/2007 | Bjellqvist | |
| 2007/0264163 A1 | 11/2007 | Hochstrasser et al. | |
| 2007/0264164 A1 * | 11/2007 | Hochstrasser | B01L 3/5085 422/400 |
| 2008/0026451 A1 * | 1/2008 | Braman | C12N 15/1006 435/270 |
| 2008/0145272 A1 | 6/2008 | Feaster et al. | |
| 2009/0017470 A1 | 1/2009 | Liu et al. | |
| 2009/0069200 A1 * | 3/2009 | Yu | B01L 3/5025 506/40 |
| 2009/0103086 A1 | 4/2009 | Stark et al. | |
| 2009/0311141 A1 | 12/2009 | Park et al. | |
| 2010/0233734 A1 * | 9/2010 | Hobbs | G01N 33/54393 435/7.24 |
| 2011/0123985 A1 | 5/2011 | Lau et al. | |
| 2011/0306122 A1 * | 12/2011 | Moritz | B01L 3/5085 435/325 |
| 2012/0077261 A1 | 3/2012 | Hirose et al. | |
| 2012/0329163 A1 | 12/2012 | Faber et al. | |
| 2013/0065771 A1 | 3/2013 | Oroskar et al. | |
| 2013/0079253 A1 | 3/2013 | Belgrader et al. | |
| 2013/0146515 A1 | 6/2013 | Bai et al. | |
| 2013/0146520 A1 | 6/2013 | Bai et al. | |
| 2013/0153422 A1 | 6/2013 | Haralampu | |
| 2013/0157380 A1 | 6/2013 | Zhou et al. | |
| 2013/0184685 A1 | 7/2013 | Buffet et al. | |
| 2013/0331787 A1 | 12/2013 | Kraus | |

FOREIGN PATENT DOCUMENTS

| | | |
|---|---|---|
| EP | 0253579 B1 | 3/1990 |
| EP | 0451686 A2 | 10/1991 |
| EP | 0313833 B1 | 1/1993 |
| EP | 0605828 A1 | 7/1994 |
| EP | 2810753 * | 12/2014 |
| WO | WO 89/03044 A1 | 4/1989 |
| WO | WO 92/16294 A1 | 10/1992 |
| WO | WO 98/43083 A1 | 10/1998 |
| WO | WO 00/66268 A1 | 11/2000 |

OTHER PUBLICATIONS

Yang, et al. "10. Superporous agarose beads as a solid support for microfluidic immunoassay" Ultramicroscopy, 108 (2008)1384-1389.

Ho, et al. 11. "Development of a novel bead-based 96-well filtration plate competitive immunoassay for the detection of Gentamycin" 49 (2013) 126-132.

Thiruppathiraja, et al. "Point-of-Care Vertical Flow Allergen Microarray Assay: Proof of Concept" Clinical Chemistry 60:9, 1209-1216 (2014).

* cited by examiner

METHOD AND APPARATUS FOR BIOMOLECULE ANALYSIS

CROSS REFERENCE TO RELATED APPLICATIONS

This application claims the benefit under 35 U.S.C. §119 (e) of U.S. Provisional Application No. 61/994,645, filed on May 16, 2014, which is incorporated by reference in its entirety.

FIELD

Disclosed are novel apparatus and uses thereof in biomolecule analysis. Particular embodiments contemplate membrane, cell or bead-based biomolecule analysis, where after a biochemical reaction such as an enzymatic reaction or an affinity binding, the signals carried by the membranes, cells or beads are to be analyzed to determine the result of the assay.

BACKGROUND

Microspheres, microparticles, or beads, have become an important form of solid state substrate for detecting, analyzing and identifying a wide range of biomolecules. Advantages of using microspheres compared to traditional plate-based assay methods include their large surface area, easiness of mixing with a solution and re-collecting, availability of different chemistry to functionalize the beads and control the density and orientation of the reactive ligands on the beads. Preparation of the beads can be easily scaled up with consistent quality of beads. Different types of microspheres can be selected based on specific requirements of the assay protocol and signal detection method. Among the most widely used microspheres, there are silica beads, magnetic beads, polystyrene beads and latex beads.

In a typical bead-based assay, for example, magnetic bead-based immuno-assay, magnetic microspheres functionalized with a specific capture antibody will be first incubated with a fluid sample in which the suspect antigen may present, and then a solution of detection antibody conjugated with an enzyme, and finally solution of enzyme substrate to generate a detectable signal. During the process, in between different incubations, stringent washing of the beads are critical for accurate results. Bead washing is normally accomplished by repeated cycles of bead collection, aspiration, and re-suspension, through centrifugation, magnetic aggregation, or vacuum assisted filtration. All of these methods are lengthy, repetitive, and need extra equipment operation. After the assay, recollecting and measuring the signals of the microspheres is also a big challenge, especially for assays using small amount of beads and multiple washing steps, because loss of beads is inevitable in most cases. Similar protocols are used for many cell-based assays to examine the biomolecules on the cell membrane or inside the cells. Commonly used lab tools include multiwell filtration devices which utilize vacuum or centrifugation force to extract the liquid out of the filtration well.

Dot blot is another widely used membrane-based biomolecule analysis method. In this format, typically, one or more specific biomolecules such as antibodies, antigens, and nucleic acids, are immobilized on a porous membrane in an array of small confined area. The blotted membrane is then placed in a serial of buffer and solutions for membrane blocking, affinity binding, rinsing, and signal development. The entire process, including multiple lengthy shaking and washing steps, takes more than two hours or even overnight to finish. A commonly used apparatus for dot blot assay relies on a vacuum source to suck solution through the membrane, but the apparatus set up is complicated, expensive, and need to be assembled, disassembled and cleaned for every use. Only a limited number of membranes can be processed using such device. Cross-contamination is hard to avoid in these methods because one continuous piece of membrane is used for multiple assay dots. Therefore, there are needs in the art for apparatus and methods that can simplify the washing and shorten the total assay time for both high throughput analysis platform and rapid test for a few samples in research and clinical labs.

SUMMARY OF THE INVENTION

The present disclosure describes an apparatus or a device and its usage for quick and efficient collection of beads and wash of the beads and for signal detection in a bead-based biomolecule analysis. The same apparatus or device can also be applied for cell-based analysis and membrane-based dot blot assays. Advantageously, the apparatus and methods of the present disclosure simplify the washing step without using centrifuge, vacuum, or magnetic force; provide more efficient washing with less volume of buffer and less time; are capable of condensing the beads and biomolecules in a small detection area to generate stronger signal; use significantly less amount of assay reagent than traditional assays; and enable quantitative signal detection and analysis using a plate reader or an imaging device.

In certain embodiments, each apparatus comprises one or more individual devices assembled in a plate. Each device has a sample well with an upper opening, bottom opening, and an inner wall, such as a sloped wall or a tapered wall for a user to introduce the bead suspension, sample solutions and additional solution into the device, and for the beads to aggregate in the detection zone at the bottom of the well for detection.

A filter membrane covers the bottom opening of the sample well. Microspheres can be retained on the upper surface of the filter membrane by size-exclusion. In some embodiments, biomolecules can be immobilized on the membrane by adsorption or other means. Preferably, the filter membrane is made of porous hydrophilic material so that aqueous solutions containing biomolecules can pass through the membrane by capillary force and gravity, without other external force.

The device further contains an absorbing plug placed in close contact with the filter membrane. The absorbing plug is made of hydrophilic porous material, which allows its rapid absorbance of aqueous solution through the filter membrane into the plug by capillary force.

Each device is individually enclosed and therefore cross-contamination is totally eliminated. Multiple devices can be arranged in an array format, such as the ANSI/SLAS 2-2004 standard 96 well format. For more flexible use, one or multiple devices pre-assembled together in an array strip or block can be inserted into a plate frame by the user.

A bead-based or cell-based assay can first be performed in a separate container for necessary mixing, incubation and any other necessary process. The user can then transfer the solution containing the beads or cells to the device. Because of the tapered wall of the sample well, the beads will aggregate at the bottom of the well while the solution is absorbed by the filter membrane and the absorbing plug by capillary force. To rinse off the unbound molecules from the beads or cells, a certain volume of the rinsing buffer is added to the well, and it will be absorbed by the absorbing plug. Multiple washing steps can be performed as long as the total volume of solution added into the device does not exceed the maximum pore volume or absorbing capacity of the absorbing plug. Besides washing, additional solution such as enzyme substrates can be added into the sample well to allow reaction to occur on the beads or cells inside the detection zone. Optionally, to reduce non-specific binding, the user can add blocking buffer onto the filter membrane before introducing the beads or cells into the device.

In a membrane-based assay, the user can first blot the agent to be immobilized onto the membrane inside the sample well and let it dry. Afterwards, the user can sequentially add blocking buffer and other reaction solutions such as antibodies and enzyme substrates into the well and let them go through the blotted membrane by capillary force and react with the immobilized molecules. Incubation time can be adjusted by the user for optimal result.

In cell, bead, or membrane-based assays using the device as described in this invention, multiple samples and plates can be processed at the same time manually or automatically. At the end of the assay, the entire plate can be analyzed visually or by a signal detecting means or instrument such as plate reader or imaging instrument. The used devices are not reusable and can be disposed properly.

The features, aspects, and advantages of the present invention will become better understood with reference to the following description.

BRIEF DESCRIPTION OF THE DRAWINGS

The present disclosure, as defined in the claims, can be better understood with reference to the following drawings. The drawings are not all necessarily drawn to scale, emphasis instead being placed upon clearly illustrating principles of the present invention.

FIG. 3A: 8×12 array, 96 well whole plate. FIG. 3B: 8×12 array, 96 well plate individual insert. FIG. 3C: 8×1 strips in 96 well plate frame. FIG. 3D: 1×12 strips in 96 well plate frame. FIG. 3E: 6×8 array, 48 well plate format. FIG. 3F: 4×6 array, 24 well plate format.

FIG. 10A: the spot, block and probe steps in the chemiluminescent dot blot assay. FIG. 10B: the incubation, rinsing and detect steps in the chemiluminescent dot blot assay.

DETAILED DESCRIPTION OF THE INVENTION

The present invention is related to laboratory apparatus used in biomolecule analysis on cell, beads, or porous membranes. After a biochemical reaction such as an enzymatic reaction or an affinity binding, the signals carried by the membranes, cells or beads are to be analyzed to determine the result of the assay.

Figure 1:
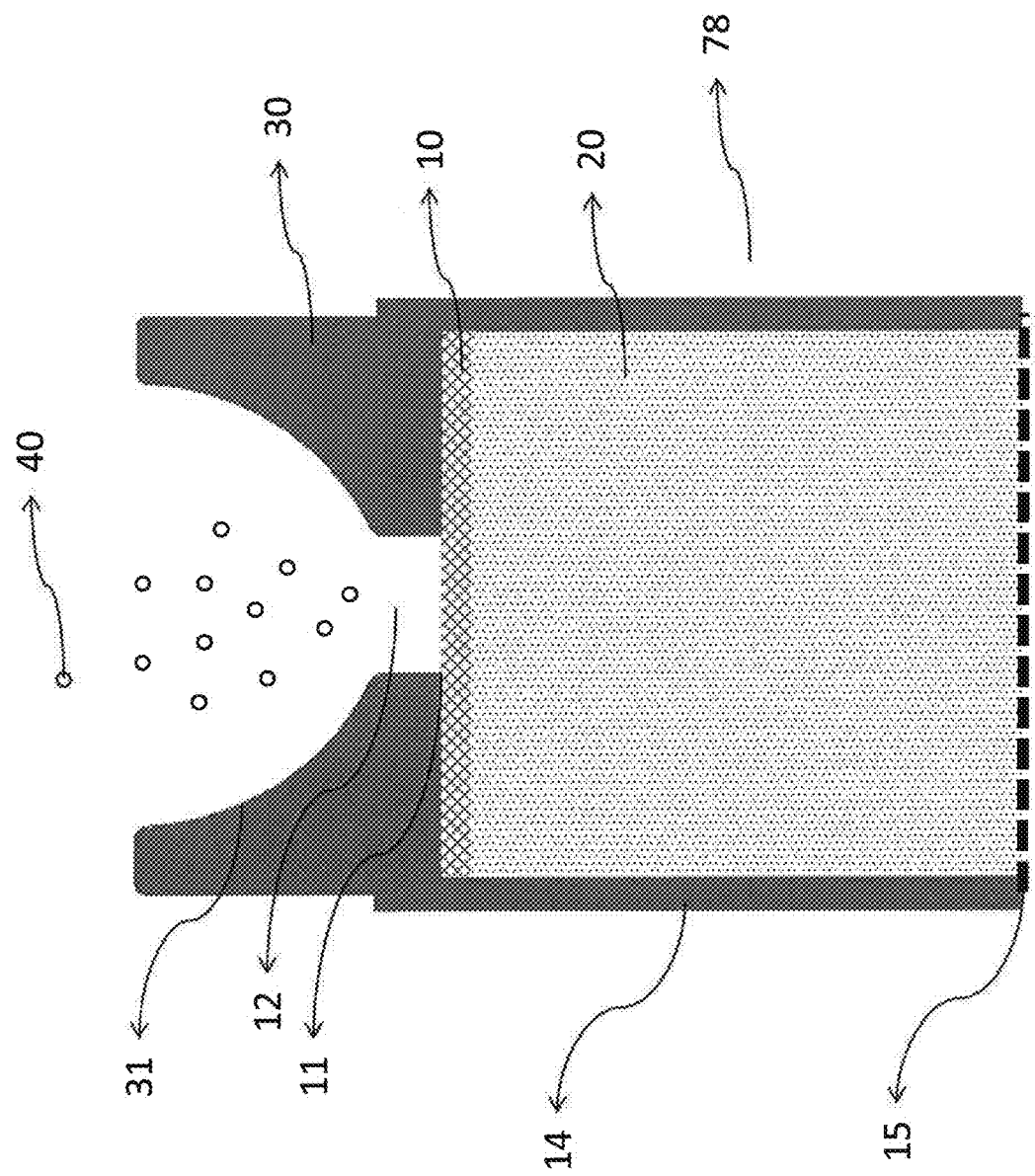
FIG. 1 is a schematic illustration of the cross-section of a single device unit.

As shown in FIG. 1, an individual device 78 described in this invention comprises a sample well 30, a filter membrane 10, and an absorbing plug 20. All three parts are assembled together inside a housing 14.

The sample well 30 is for addition of sample and other solutions into the device. The dimension of the well will vary for different applications but typically ranges from 3 to 30 mm in diameter and 3 to 30 mm in height. In some embodiments, the dimension of the well is from 6 mm to 18 mm in diameter and 4 mm to 10 mm in height. The cross-section of the well can be circular, elliptical, square, rectangular, pentagonal, hexagonal, octagonal, or any other shapes. The well has a sloped inner wall 31 to guide the solution flow toward the bottom of the well by gravity. The bottom of the well is open to the second component filter membrane 10, and forms a detection zone 12 for the beads to aggregate, or in some embodiments, for the biomolecules to be immobilized on the filter membrane. The detection zone 12 is preferably cylindrical shaped to ensure a uniformed distribution of the beads when they aggregate on top of the filter membrane 10. In preferred embodiments, the detection zone is 0.5-7 mm in diameter and 0.5-2 mm in height. The diameter and height of the detection zone can be varied to hold different volume of beads for different applications. The well is made of a low fouling material such as a polymer or a copolymer, e.g., polypropylene or poly (methyl methacrylate) (PMMA) to minimize non-specific biomolecule adhesion. The well can be transparent or opaque. For fluorescence and luminescence detection, opaque material is preferred to minimize external light interference.

The second component 10 is a filter membrane, or a porous membrane, whose pore size is selected to be smaller than the size of the microspheres to be used in a bead-based bioassay. The filter membrane is capable of preventing the passage of microspheres whose diameters are bigger than the filter membrane's pore size, and at the same time allowing the passage of the aqueous solution and particles smaller than the filter membrane's pore size. In some embodiments, the membrane has a pore size between about 0.3 µm to about 50 µm. The pores in the membrane can be randomly or uniformly distributed. In one embodiment, the membrane has pores with a uniform size with a certain variance. Any hydrophilic porous organic or inorganic material can be used as the filter membrane, such as silver membrane, glassfiber membrane, nitrocellulose membrane, mixed cellulose ester (MCE) membrane, polycarbonate (PC) membrane, polyester (PET) membrane, cellulose acetate membrane, nylon membrane, polyethersulfone (PES) membrane, polyvinylidene difluoride (PVDF) membrane, regenerated cellulose (RC) membranes etc. Some intrinsically hydrophobic material can be treated to become hydrophilic, such as porous polyethylene (PE) and polypropylene (PP), and can also be used as filter membrane. Thickness of the membrane can be from about 10 μm to 10 mm. In some embodiments, the thickness of the membrane is from about 100 μm to about 1 mm. The terms "pore" and "void space" are used interchangeably.

The filter membrane can be used without further treatment, or can be further processed to alter its surface property. In certain embodiments, to facilitate the passage of free bio-molecules such as proteins and peptides through the filter membrane, the filter membranes have low protein binding surface. Membranes made of low fouling materials, such as polyethersulfone (PES), cellulose acetate, and regenerated cellulose (RC), can be used directly without additional treatment. In certain instances, such membranes and other membranes with higher protein-binding capabilities, such as glassfiber, nitrocellulose, nylon, and mixed cellulose ester (MCE), can be treated with bovine serum albumin (BSA) or other commercially available blocking solutions to reduce non-specific protein adsorption.

In one instance, the disc filters are first soaked with Superblock blocking buffer from Thermo Scientific for 8 hours and then rinsed with distilled water and dried in air at 55° C. for 24 hours.

For fluorescence detection, the filter membrane should have low auto-fluorescence in the signal detection wavelength region to minimize the background. For colorimetric and luminescence analysis, membranes with white appearance would be preferred.

In a preferred embodiment, the filter membrane is a 0.3-0.7 mm thick, glassfiber disc filter with pore size range from 0.3 to 2.7 μm. In one embodiment, the filter membrane is a 0.3-0.5 mm thick glassfiber disc filter with 0.7 μm pore size. In one embodiment, the filter membrane is a 0.3-0.5 mm thick glassfiber disc filter with 1.6 μm pore size. In another embodiment, the filter membrane is a 0.3-0.7 mm thick glassfiber disc filter with 2.7 μm micrometer pore size.

In another preferred embodiment, the filter membrane is a nitrocellulose or mixed cellulose ester (MCE) membrane with pore size range from 0.5 to 5.0 μm. In one embodiment, the filter membrane is a 0.1-0.2 mm thick MCE membrane with 1 μm pore size. In one embodiment, the filter membrane is a 0.1-0.2 mm thick MCE membrane with 3 μm pore size. In another embodiment, the filter membrane is a 0.1-0.2 mm thick MCE membrane with 5 μm pore size.

In another preferred embodiment, the filter membrane is a nylon membrane with pore size range from 0.5 to 5.0 μm. In one embodiment, the filter membrane is a 0.05-0.2 mm thick nylon membrane with 5 μm pore size. In one embodiment, the filter membrane is a 0.05-0.2 mm thick MCE membrane with 10 μm pore size. In another embodiment, the filter membrane is a 0.05-0.2 mm thick MCE membrane with 20 μm pore size.

The filter membrane can be bigger than the well bottom opening 11, and in close contact with the edge of the bottom well opening to effectively block the microspheres or liquid from leaking through. This can be achieved by general bonding method or by support from the components placed underneath the membrane. In one instances, the support is from the absorbing plug 20 through the friction force generated between the absorbing plug and the housing 14.

The third component is an absorbing plug 20 in contact with the filter membrane. Any hydrophilic absorbent material can be used as an absorbing plug, such as glassfiber, cellulose acetate fibers, sponge, foam, cotton, porous polymers or polymer fiber, such as polyethylene (PE) and polyester (PET) etc. There is no restriction on the pore size of the absorbing plug 20, and it can be larger than the pore size of the filter membrane 10. It would be preferred that the absorbing plug has a large pore size so that it will have a large maximum absorbing capacity, allowing a large volume of solution added into the device. Preferably the absorbing plug is low-fouling so that free biomolecules will have minimum adsorption on the pores while going through the absorbing plug. The low protein-binding characteristic of the absorbing material is critical for low background detection. Preferred materials include glassfiber, porous PE, and porous PE/PET sheath/core bonded fiber. In preferred embodiments, the selected material has between 30% to 90% pore volume. In one embodiment, the absorbing plug is made of porous PE/PET sheath/core bonded fiber with 60-80% porosity and fiber direction perpendicular to the face in contact with the filter membrane. In another embodiment, the absorbing plug is made of hydrophilic porous PE with 60% porosity. Depending on the application and size of the device, the total liquid absorbing capacity of the absorbing plug is from about 10 μl to 50 ml.

Figure 2B:
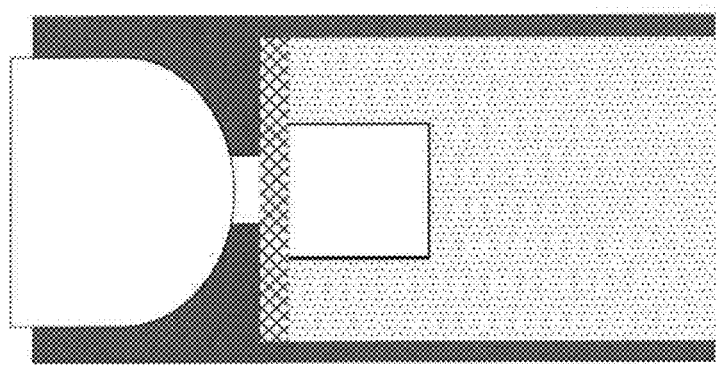
FIGS. 2A-2E are schematic illustrations of examples of different geometric designs of the absorbing plugs in a single device.
Figure 2A:
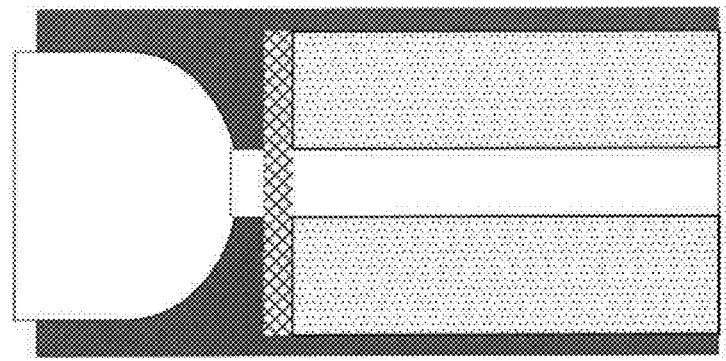
Figure 2C:
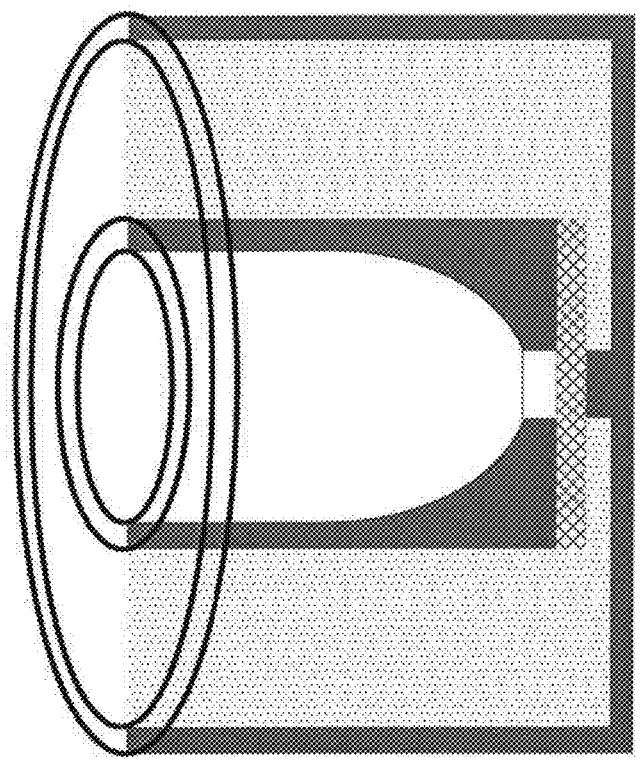
Figure 2D:
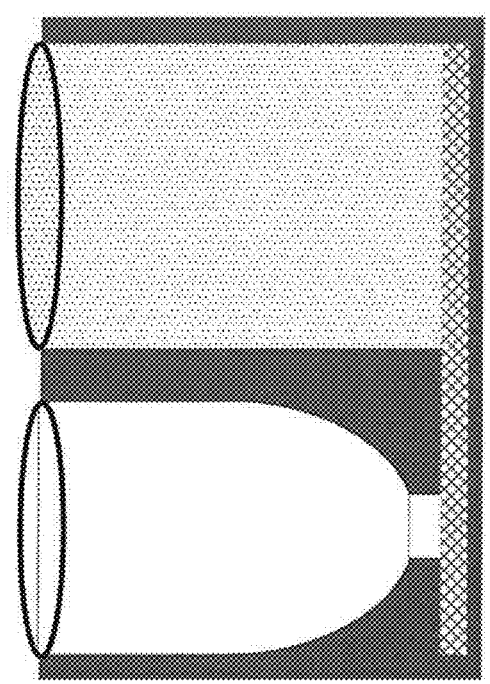
Figure 2E:
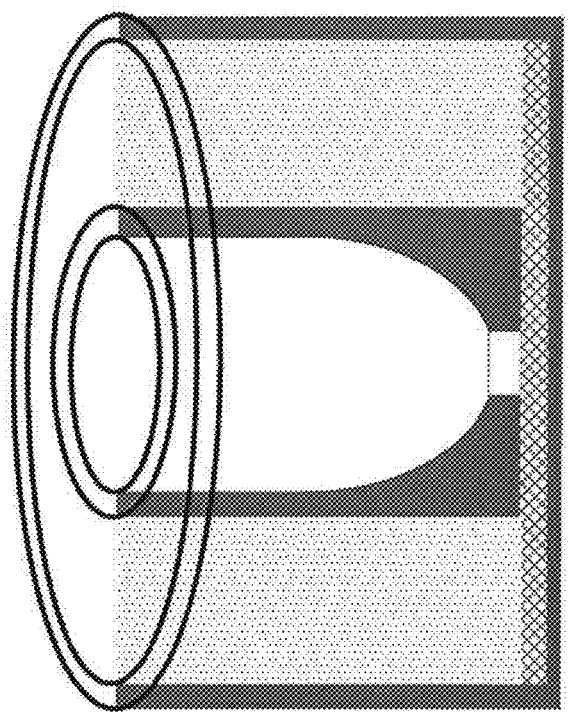

The absorbing plug is assembled in close contact and in fluid communication with the filter membrane. Once the filter membrane is saturated by the aqueous solution added into the device, the aqueous solution will pass through the filter membrane and enter the absorbing plug by capillary force. Both the contacting position and the shape of the absorbing plug can be varied. The contact position can be under the filter membrane as shown in FIG. 1 and FIGS. 2A-2C, or above the membrane outside the sample well, as shown in FIGS. 2D and 2E. If the contact is under the filter membrane, a void can be created in the plug under the lower well opening 11 and detection zone 12, as shown in FIGS. 2A-2C. The cross-section of the void has a dimension equal or larger than the lower well opening 11 and detection zone 12, and a height range from about 1 mm to the height of the absorbing plug under the membrane. The embodiment, where part of the absorbing plug has no direct contact with the filter membrane right under the lower well opening 11 and detection zone 12, has the advantage of reducing the signal background in the detection zone. The designs in FIG. 1 and FIG. 2 are only examples, not to limit the scope of the invention.

Different shapes of the absorbing plug can be used. In some embodiments, the absorbing plug has a shape selected from cylindrical, cubical, rectangular prism or polygonal prism. Size of the absorbing plug can be selected to accommodate the total volume of liquid needed to be processed in the assays. In one preferred embodiment, the absorbing plug has a cylindrical shape (7 mm diameter×14 mm height). In another preferred embodiment, the absorbing plug has an 8 mm×8 mm×8 mm cubic shape. In another embodiment, the absorbing plug is a 16 mm width×16 mm length×10 mm height block.

Since both the filter membrane and the absorbing plug are porous material, they can be made of one or more layers of the same or different materials or even merge into one piece. For example, a device can have a porous PE frit as the filter membrane and a porous PE rod as the absorbing plug. In another example, a device can have multiple layers of glassfiber discs, with the top one or more layer(s) serving as the filter membrane and the lower ones as the absorbing plug. In another example, a device can have one single rod of PE working as both the filter membrane and the absorbing plug. In some embodiments, the absorbing plug can be made with multiple layers of porous material, with each layer having the same or different material, pore size, property, thickness, and/or shape. In some embodiments, the 1-piece absorbing plug can have different material properties, such as pore size, in different area.

The three components of the device, sample well, filter membrane, and absorbing plug, are hold together in close contact by friction force or by any bonding method, including, but not limiting to welding or adhesion, inside an enclosing housing 14 (FIG. 1). The housing can be made of a single piece of plastic material such as polypropylene (PP) or poly(methyl methacrylate) (PMMA) by injection molding, or multiple parts assembled together by adhesion, welding, or any other bonding method. In a preferred embodiment, the housing and the sample well is made in one piece of PP or PMMA by injection molding. And the filter membrane and absorbing plug is fixed inside the housing under the sample well by friction force. Other than the upper well opening 11, the case should have at least one other air permeable opening that can provide ventilation for the absorbing plug 20. In a preferred embodiment, as shown in FIG. 1, the bottom of the absorbing plug is sealed inside the housing 14 with an air permeable hydrophobic membrane 15, such as the hydrophobic acrylic copolymer membrane from Pall Corporation. In another preferred embodiment, the bottom of the absorbing plug is open to air.

Figure 3A:
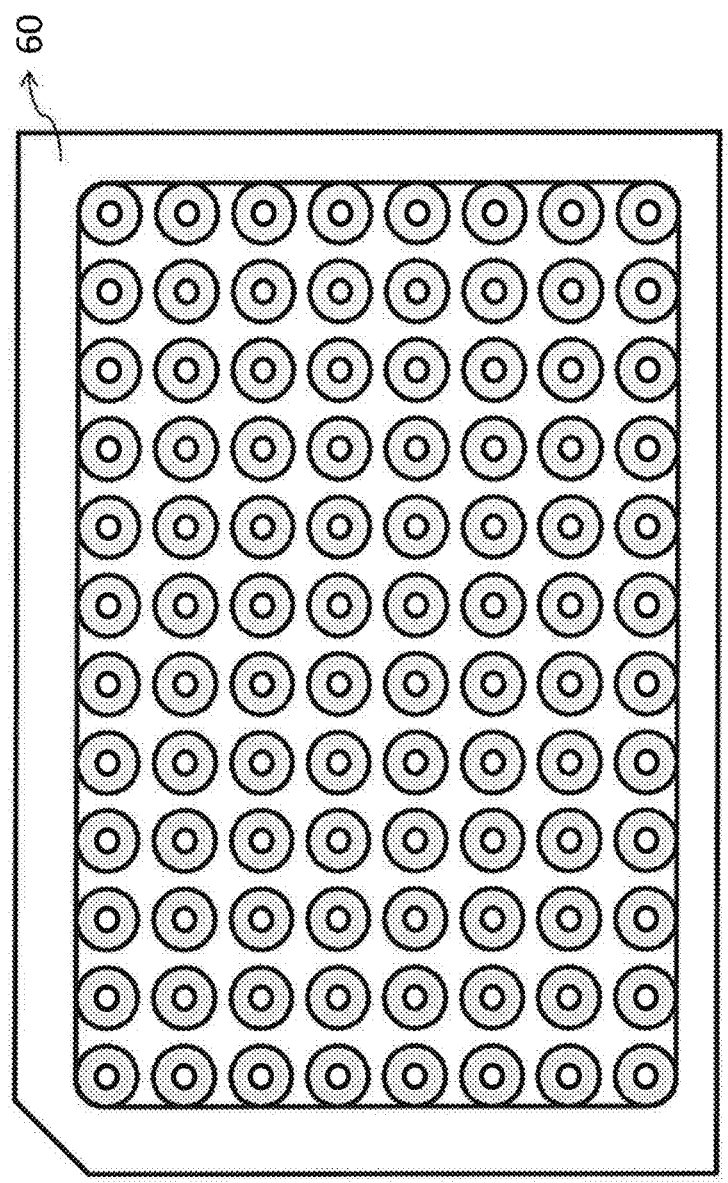
FIGS. 3A-3F are schematic illustrations of examples of arrangement of multiple devices in a plate format.
Figure 3B:
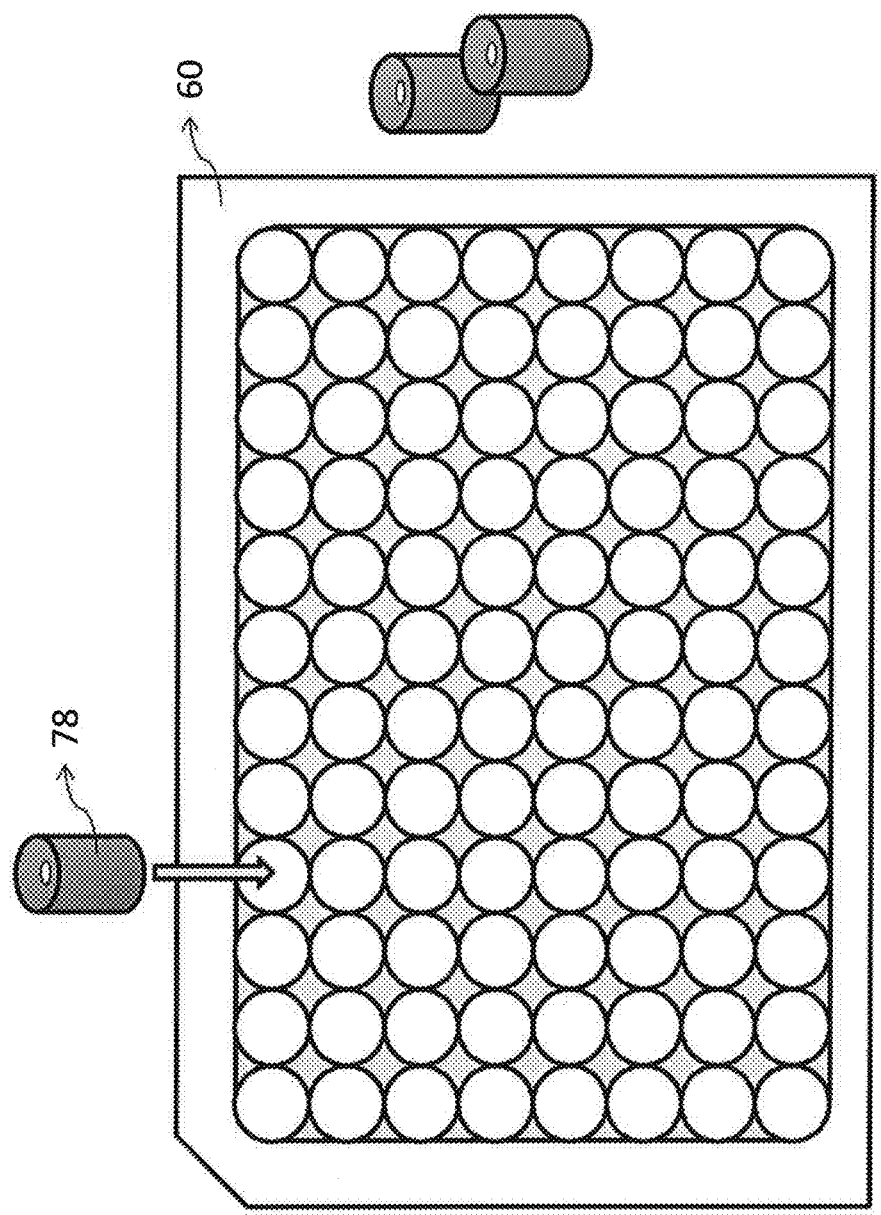
Figure 3C:
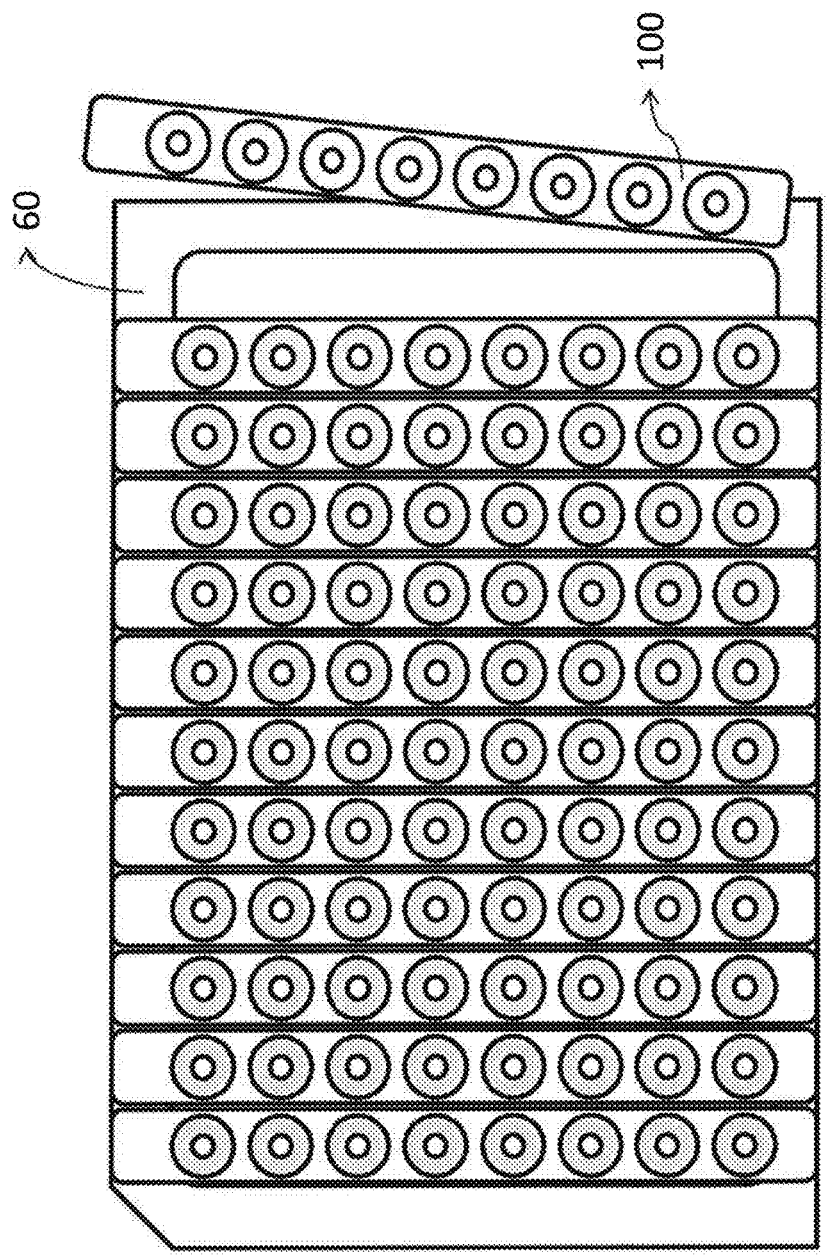
Figure 3D:
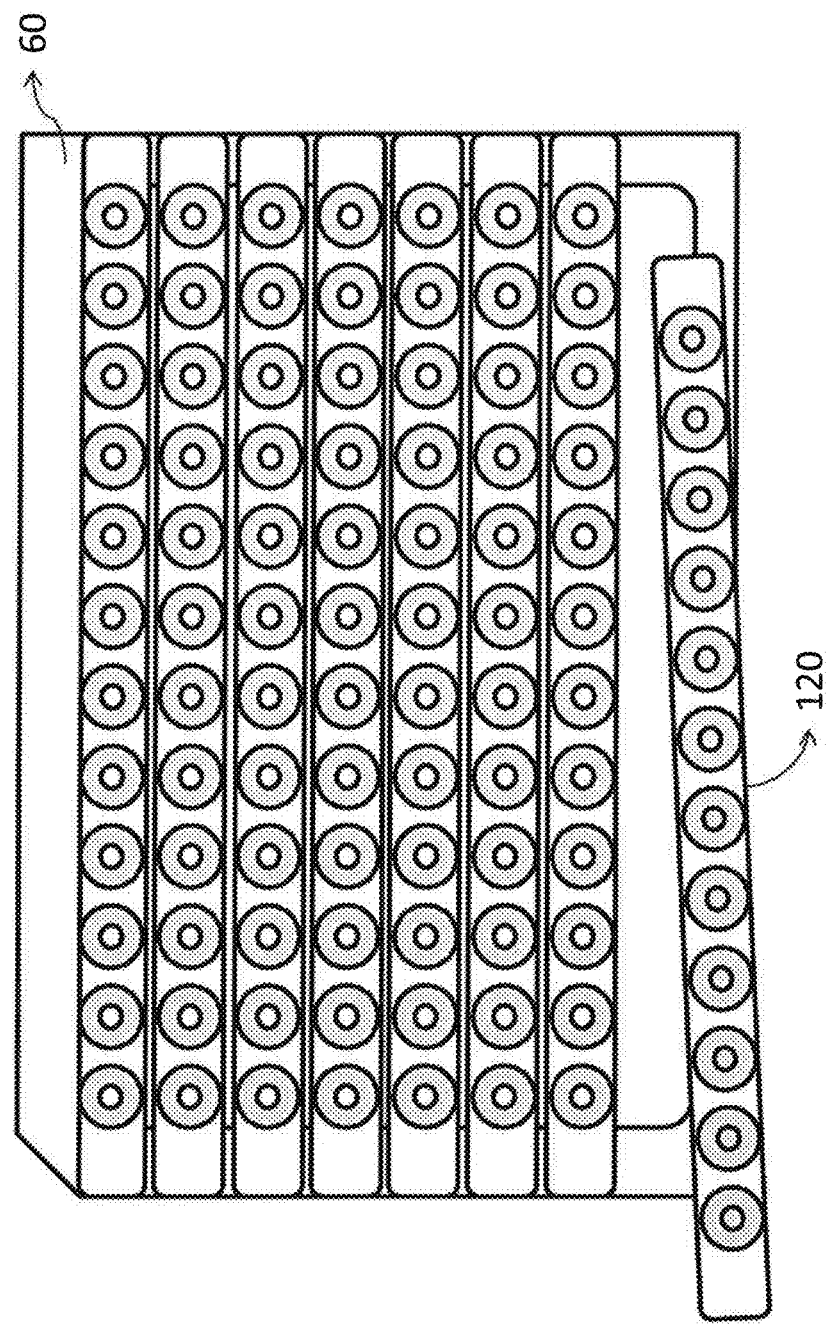
Figure 3E:
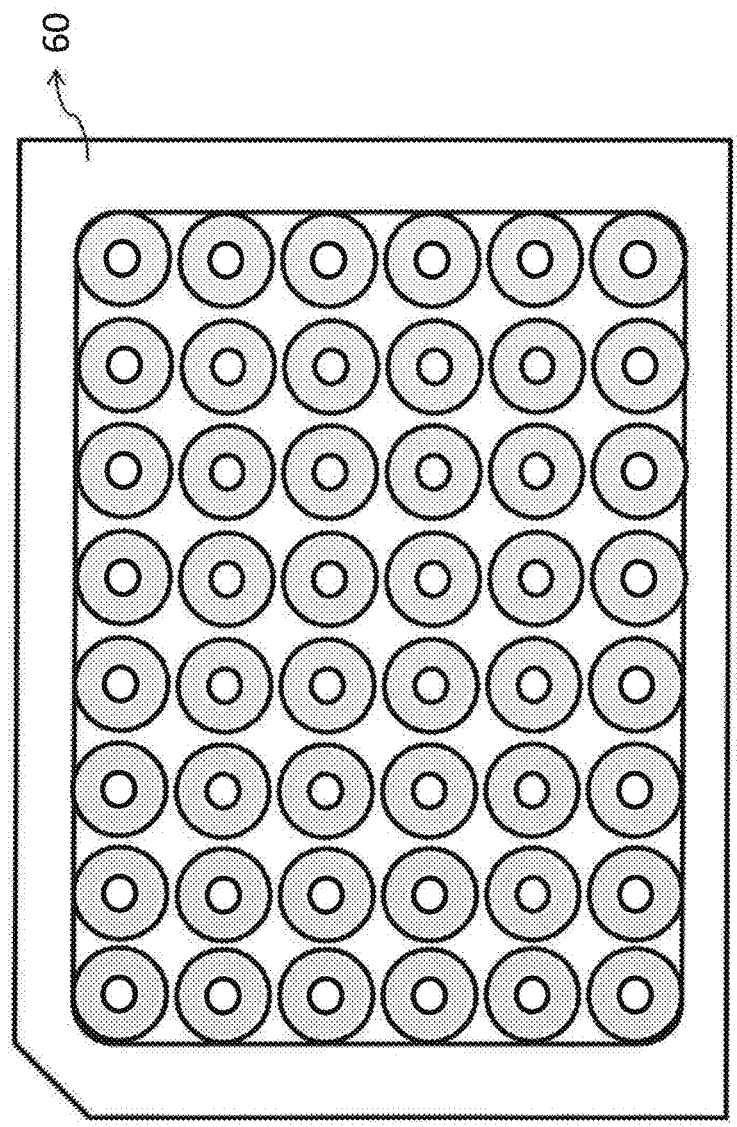
Figure 3F:
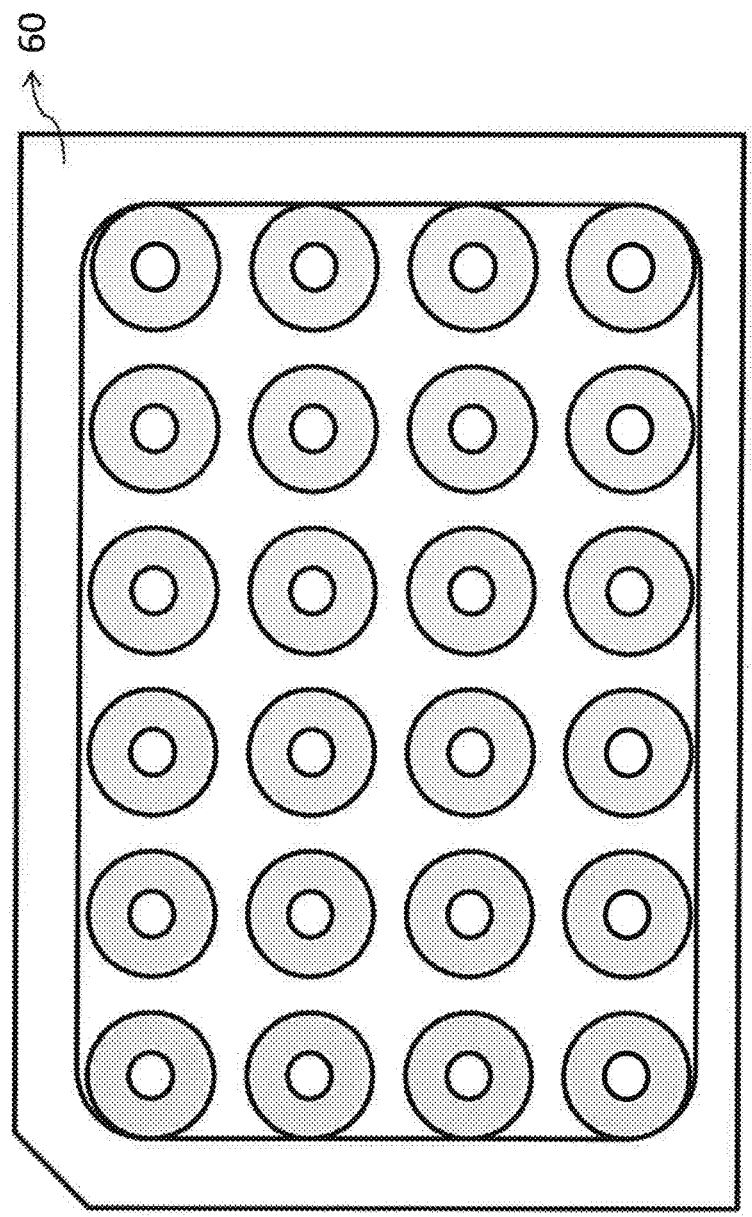
Figure 4:
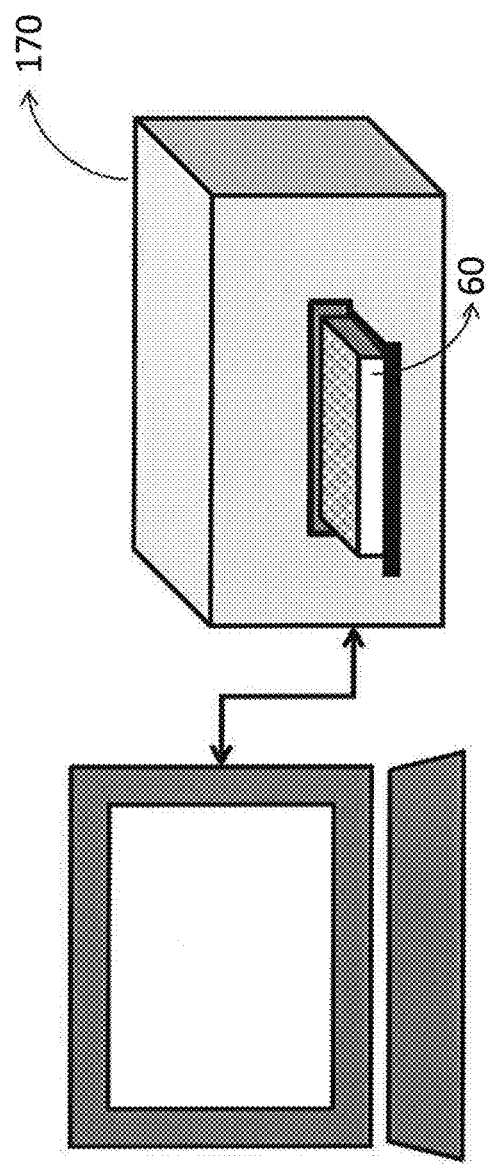
FIG. 4 is a schematic illustration of how the signal generated in the apparatus after a biological assay can be detected by a plate reader.

In order to be compatible with commonly-used plate reader for signal detection and analysis, multiple devices are arranged in a plate 60 in a rectangle array format such as 8×12 (FIGS. 3A-3D), 6×8 (FIG. 3E), 4×6 (FIG. 3F), or other format that user find convenient. Individual devices 78 (FIG. 3B) or multiple devices pre-assembled in a smaller array block such as an array of 8×1 (strip 100 in FIG. 3C) or 1×12 (strip 120 in FIG. 3D) devices, can be inserted into the plate by the user. The plate containing one or more devices can be inserted into a plate reader or an imaging instrument 170 for signal detection (FIG. 4), and be processed in a robotic high throughput work station. In a preferred embodiment, the footprint of the plate conforms to the ANSI/SLAS 2-2004 standard 96 well format, with 127.76 mm length, 85.48 mm width, 14.35 mm height, and 9.0 mm inter-well distance. In another preferred embodiment, the footprint of the plate has 127.76 mm length, 85.48 mm width, and 12.0 and 18.0 mm inter-well distance for 48 well (6×8 array) and 24 well (4×6 array) plate respectively. In certain embodiments, as used herein, the inter-well distance means the distance between the centers of two adjacent wells or devices.

Figure 5:
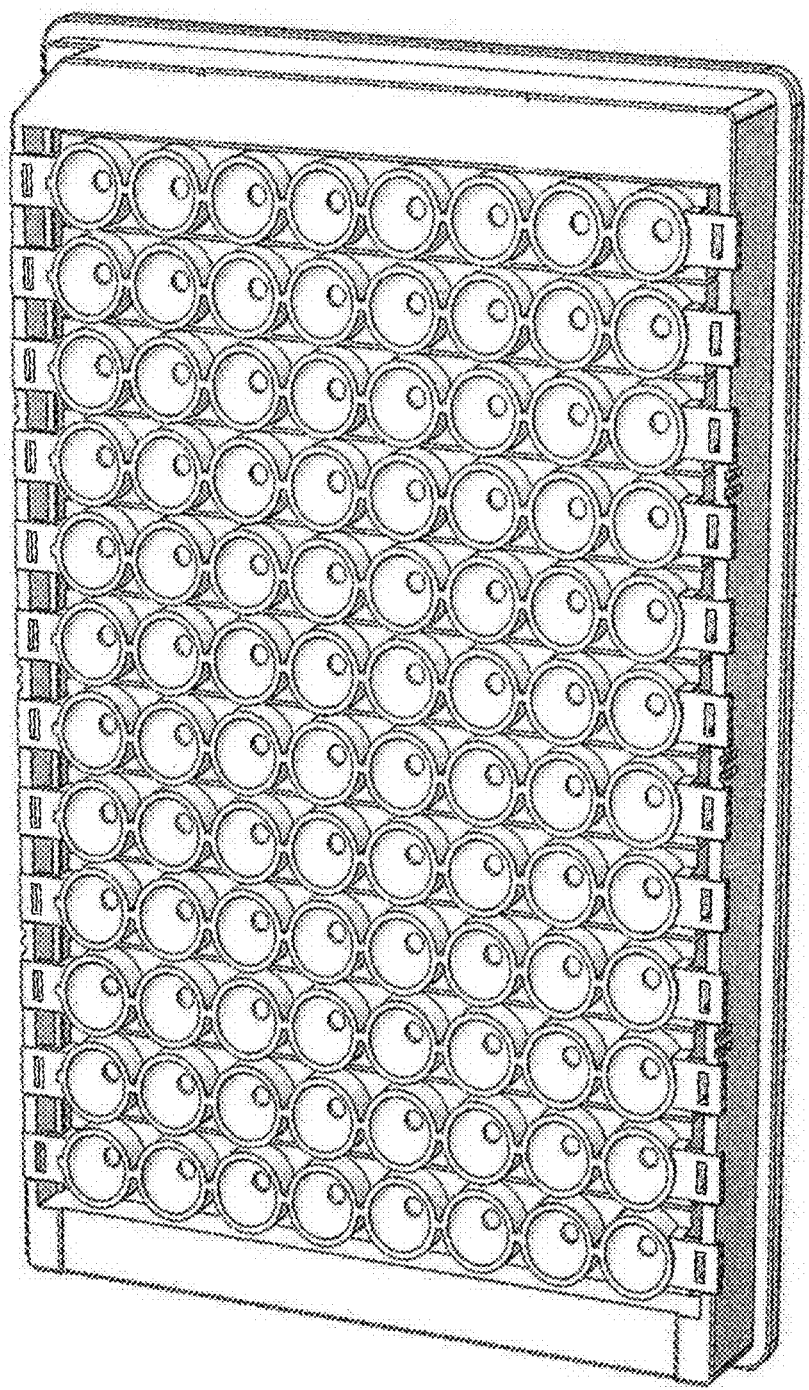
FIG. 5 is an embodiment of the invention.

An embodiment of the device described in this invention is shown in FIG. 5. One to twelve 8-well strips each containing 8 units of the devices can be inserted into a strip holder frame, which conforms to the ANSI/SLAS 2-2004 standard 96 well format [127.76 mm length×85.48 mm width×14.35 mm height]. Inter-well distance is 9.0 mm. The 8-well strips are made of opaque PMMA by injection molding. Each sample well has a round upper opening with diameter 7.0 mm. The well is 3.5 mm in height and has a curved wall. The bottom of the well has a detection zone 2 mm in diameter and 0.65 mm in height. The filter membrane under the detection zone is a borosilicate glassfiber membrane with pore size of 0.7 μm and thickness of 0.5 mm. The absorbing plug under the glassfiber membrane is a porous PE/PET fiber cube 8.0 mm (width)×7.6 mm (length)×8.0 mm (height) with 70% porosity.

In some embodiments, the present invention provides a method for assaying a biological sample. The method includes filtering a mixture through an apparatus or a device and detecting a reporter agent with an analytical means. In some embodiments, the mixture includes a plurality of functionalized beads, a sample comprising a target analyte, and a detectable reporter agent. In some embodiments, the mixture includes a plurality of functionalized beads, and a sample comprising an analyte, which by itself is a reporter agent capable of producing detectable signals. The device includes a filtering member having an upper surface and a lower surface; a sample well comprising a top opening for sample addition and a bottom opening, where the bottom opening of the sample well is disposed on the upper surface of the filtering member and defines a detection zone; a porous absorbing member having a surface, where the surface of the absorbing member is in contact with the filtering member, and a housing, where the filtering member, the sample well and the absorbing member are disposed in the housing.

In some embodiments, provided is a method for assaying a sample. The method includes providing a device as described herein; optionally adding a blocking buffer to the filter membrane of the device; filtering a mixture of beads and other reagents through the filter membrane from the sample well in the device; adding rinsing buffer into the sample well in the device and let the liquid be absorbed by the absorbing plug in the device; optionally adding additional samples, reaction agents, and buffers into the sample well in the device and let the liquid be absorbed by the absorbing plug in the device; and detecting a signal, such as an optical or radioactive signal from the detection zone in the device.

In some embodiments, the mixture contains a plurality of functionalized beads, a sample containing a target analyte, and a detectable reporter agent, such as a labeled antibody or nucleic acid. In some embodiments, the mixture contains a plurality of functionalized beads, and a sample containing an analyte, which by itself is a reporter agent capable of producing detectable signals. In some embodiments, the reaction reagents include unlabeled biomolecules or biomolecules conjugated with an enzyme such as horseradish peroxidase (HRP) or alkaline phosphatase (AP), or a detectable agent such as fluorophores and micro- or nano-sized particles. In some embodiments, the reaction reagents include substrates for enzyme reaction to generate a detectable signal, such as chemiluminescent, chemifluorescent, and chromogenic signal. In some embodiments, the step of detecting includes visual inspection and the use of an analytical means including a plate reader or an imaging system. Exemplary plate reader includes a fluorescence plate reader or a chemiluminescence plate reader. Exemplary imaging system includes a camera or a gel imager.

In certain embodiments, provided is a method for assaying a sample. The method includes providing a device as described herein; immobilizing a labeled or unlabeled biomolecule on a section of the filter membrane of a device as described herein; adding a blocking buffer into the sample well and let the liquid be absorbed through the filter membrane by the absorbing plug of the device; adding one or more sample solution, reaction reagents and buffers into the sample well of the device and let the liquid be absorbed through the filter membrane by the absorbing plug of the device; and detecting a signal, such as an optical or radioactive signal from the detection zone of the device.

In some embodiments, the immobilizing step includes adding a solution containing a labeled or unlabeled biomolecule such as protein or nucleic acid onto the filter membrane and drying the filter membrane. In some embodiments, the immobilizing step includes adding a solution containing a labeled or unlabeled biomolecule such as protein or nucleic acid onto the filter membrane and let it incubate for a certain amount of time.

In some embodiments, the reaction reagents include unlabeled biomolecules or biomolecules conjugated with an enzyme such as horseradish peroxidase (HRP) or alkaline phosphatase (AP), or a detectable agent such as fluorophores and micro- or nano-sized particles. In some embodiments, the reaction reagents include substrates for enzyme reaction to generate a detectable signal. In some embodiments, the step of detecting includes visual inspection and the use of an analytical means including a plate reader or an imaging system. Exemplary plate reader includes a fluorescence plate reader or a chemiluminescence plate reader. Exemplary imaging system includes a camera or a gel imager.

In an example bead-based assay, the functionalized beads 40 are first mixed and incubated with appropriate biological sample and reagents to have biochemical reaction occur on the surface of the beads. As a result of the reaction, in the bead and reagent mixture, molecules that can generate a detectable signal, such as fluorescent, colorimetric or luminescent signal, are immobilized on the bead surface. To separate the beads from the solution, the mixture is added into well 30. To minimized non-specific binding of the unbound signal-generating molecules, a blocking solution such as 5% Bovine Serum Albumin can be applied to the membrane 10 prior to sample addition. As the liquid being absorbed by the filter membrane 10 and the absorbing plug 20 through the well opening 11, the beads aggregate in the detection zone 12. Additional buffer is then added into the well to further rinse the beads. The beads are now ready for signal detection. In some applications, enzyme substrates can be added into the detection zone to generate a detectable signal. Depending on the type of signal, the beads can be analyzed in different analyzers. For example, fluorescent signal can be detected in a fluorescent plate reader. Chemiluminescent signal can be detected in a luminometer plate reader with a photo-multiplier tube (PMT) or a gel imager with a CCD camera. Colorimetric signal can be directly visualized by naked eye or by measuring the color intensity using epi-white light illumination. The beads in the detection zone can also be imaged on a microscope. After use, the devices are not re-usable and can be disposed properly.

In an example membrane-based dot blot assay, a small amount (1-5 μl) of antigen to be probed is first added onto the filter membrane 10 and let incubate for 20 minutes. A blocking solution such as 10% Bovine Serum Albumin is then applied to the membrane 10 and incubates for another 20 minutes. A small amount (1-5 μl) of primary antibody is added onto the filter membrane 10. After a 5-minute incubation, unbound primary antibody is rinsed by the rinsing buffer added in to the sample well and absorbed by the absorbing plug. A small amount (1-5 μl) of secondary antibody conjugated with a detectable agent such as HRP, AP, fluorophore, or nano- or micro-sized particles is added onto the filter membrane. After another 5-minute incubation, unbound secondary antibody is rinsed by 200 μl rinsing buffer added in to the sample well and absorbed by the absorbing plug. In some applications, enzyme substrates are added into the detection zone to generate a detectable signal. Depending on the type of signal, the membranes can be analyzed in different analyzers. For example, fluorescent signal can be detected in a fluorescent plate reader. Chemiluminescent signal can be detected in a luminometer plate reader with a photo-multiplier tube (PMT) or a gel imager with a CCD camera. Colorimetric signal can be directly visualized by naked eye or by measuring the color intensity using epi-white light illumination. After use, the devices are not re-usable and can be disposed properly.

The following examples are for illustrative purposes only and the invention is not limited to the disclosed.

Example 1

Human Alpha-Fetoprotein (AFP) Fluorescence Immunoassay

Figure 6:
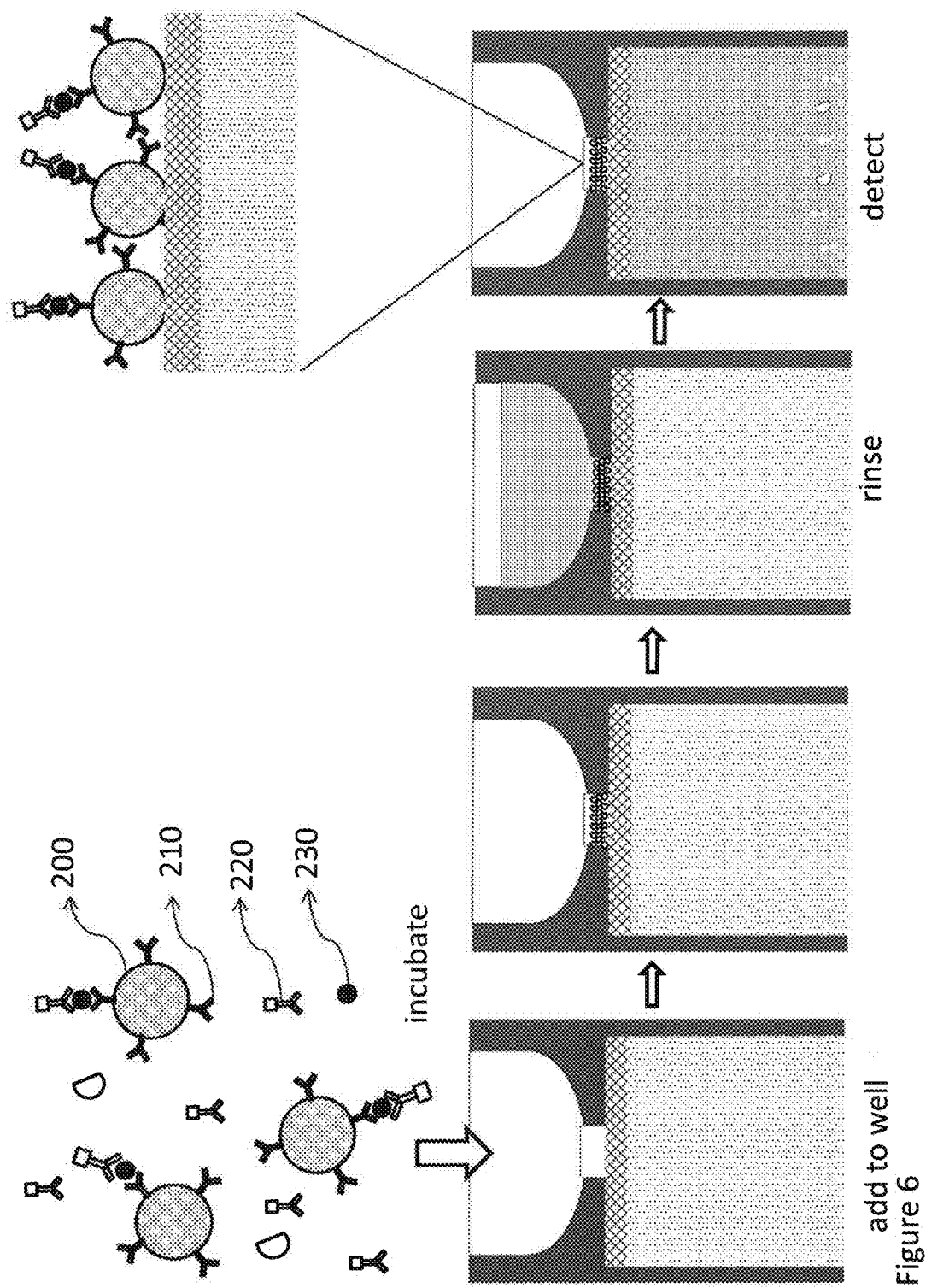
FIG. 6 is a schematic illustration of the process of a bead-based fluorescent immunoassay performed using the apparatus as described in the present disclosure.

This example shows how a device described in this invention can be used for a rapid silica bead-based fluorescent immunoassay to detect AFP from human serum sample. The process can be better understood with reference to FIG. 6.

The assay will need the following reagents: (1) silica beads 200 functionalized with AFP capture antibody 210; (2) fluorescently-labeled AFP detection antibody 220; (3) serum sample containing the target AFP molecule 230; and (4) rinsing buffer.

The capture antibody, mouse monoclonal anti-human AFP antibody, is available from R&D Systems. It can be covalently attached to 5 μm carboxylated silica beads through carboxyl-amine crosslinking reaction. Functionalized silica beads can be blocked with 10% bovine serum albumin (BSA) and stored at 1% solid in phosphate buffered saline (PBS) solution containing 1% BSA with 0.5% Tween-20 (1% BSA-PBST). The detection antibody, polyclonal chicken anti-AFP antibody can be labeled with fluorophore Alexa Fluro 647 (AF647) using commercially available labeling kits from Thermo Scientific. The rinsing buffer is 1% BSA-PBST.

For this assay, the device will have a sample well which is 6.5 mm in diameter, 3.5 mm in height, a detection zone which is 2 mm in diameter and 1 mm in height, 7 mm diameter glassfiber filter membrane disc with 2.7 μm pore size, and an 8 mm×8 mm×8 mm porous polyethylene absorbing cube with 60-70% pore volume. Devices assembled in 8-well strip format with inter-device distance of 9 mm are inserted into a 96 well plate frame. Before the assay, the glassfiber filter membrane is blocked with SuperBlock blocking buffer.

A mixture of 10 μl serum sample to be examined, 10 μl anti-AFP silica beads, and 1 μl 100 nM AF647-antiAFP antibody will be incubated at room temperature for 30 minutes. Multiple assays with different samples and positive and negative controls can be performed simultaneously. 20 μl of each assay mixture can be added into the well of a device described in this invention. After the solution is absorbed, silica beads will settle in the detection zone. To rinse, 200 μl rinsing buffer can be added into the well drop by drop using a pipette. After all the PBS buffer is absorbed, the plate can be inserted into a fluorescent plate reader for signal detection. The plate reader should be configured into a top-reading mode, with appropriate setting of excitation and emission wavelengths for AF647 detection. The reading should be obtained within 10 minutes after the rinsing buffer is fully absorbed. The concentration of AFP in the sample can be obtained by referring to a calibration curve obtained under the same assay condition using AFP standards.

Example 2

Human Alpha-Fetoprotein (AFP) Chemiluminescence Immunoassay

Figure 7:
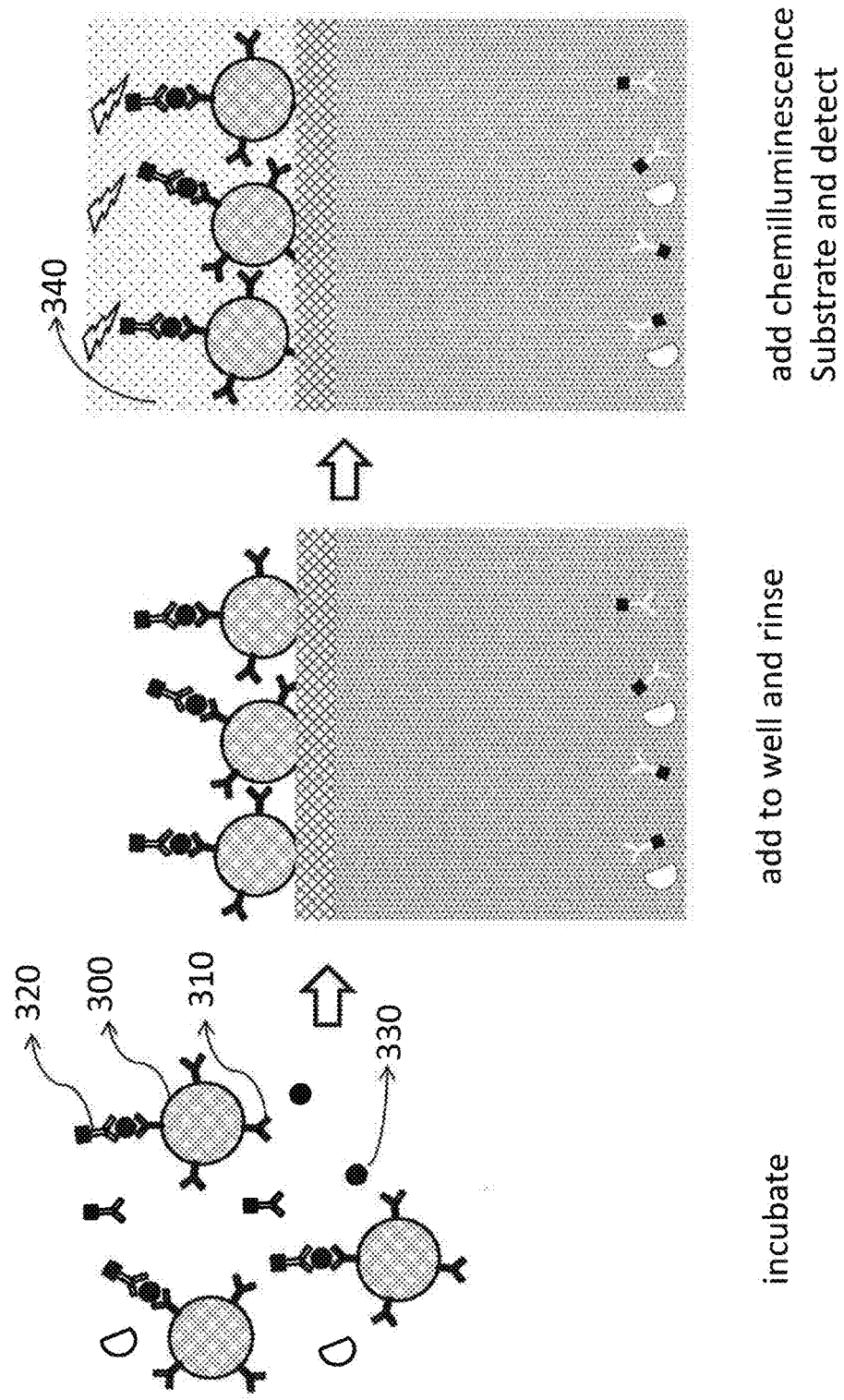
FIG. 7 is a schematic illustration of the process of a bead-based chemiluminescent immunoassay performed using the apparatus as described in the present disclosure.
Figure 8:
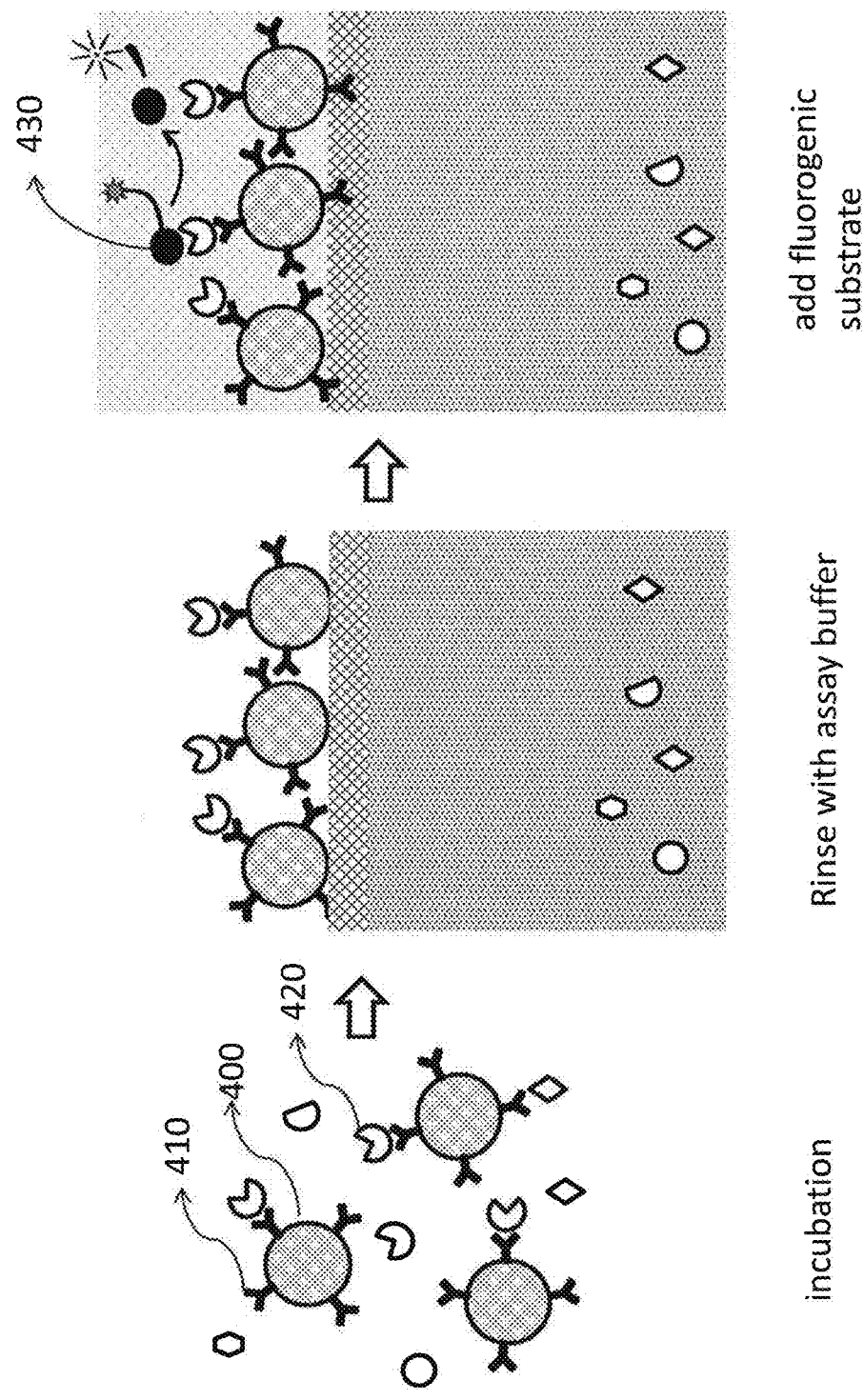
FIG. 8 is a schematic illustration of the process of a bead-based fluorescent BoNT/A activity detection assay using the apparatus as described in the present disclosure.
Figure 9:
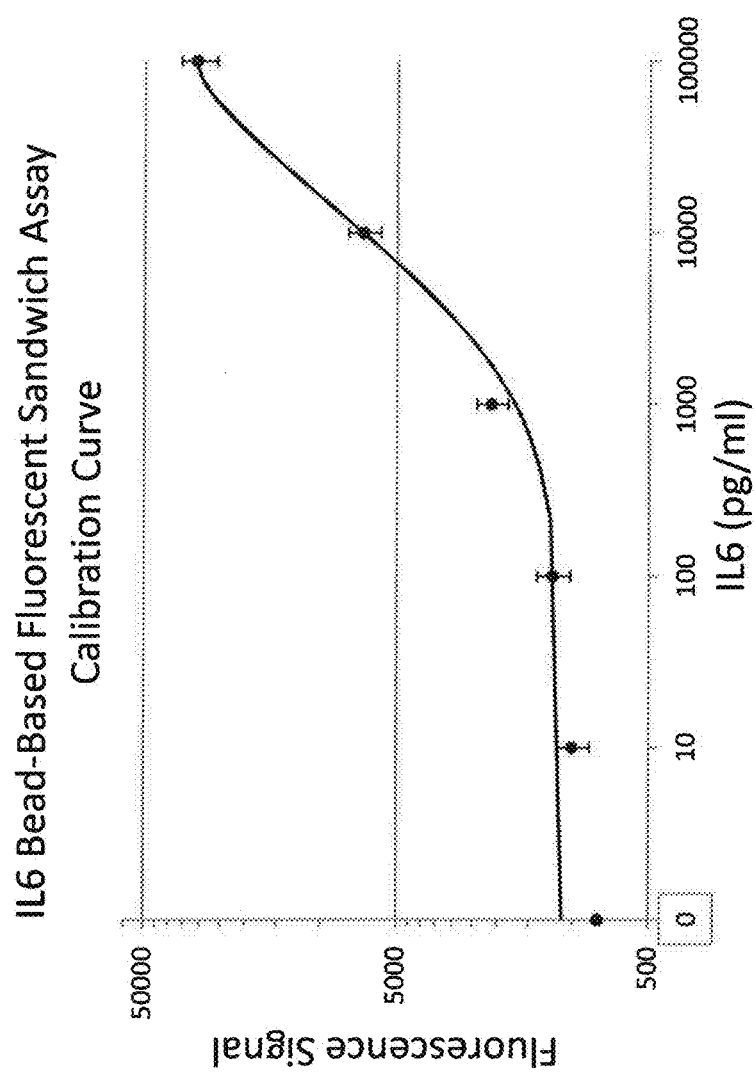
FIG. 9 is a calibration curve obtained with a bead-based assay using the apparatus as described in the present disclosure.

This example shows how a device described in this invention can be used for a rapid agarose bead-based chemiluminescent immunoassay. The process can be better understood with reference to FIG. 7.

The assay will need the following reagents: (1) Agarose beads 300 functionalized with AFP capture antibody 310; (2) AFP detection antibody labeled with horse radish peroxidase (HRP-antiAFP antibody) 320; (3) serum sample that may contain the target AFP molecule 330; (4) rinsing buffer 1% BSA-PBST; and (5) HRP chemiluminescence substrate 340.

The capture antibody, such as the mouse monoclonal anti-human AFP antibody from R&D Systems can be cross-linked to 20 μm glyoxal agarose beads through glyoxal-amine chemistry. The anti-AFP agarose beads can be stored at 20% slurry 1% BSA-PBST. The detection antibody, polyclonal chicken anti-AFP antibody can be labeled with HRP using commercially available labeling kits. In some cases, HRP conjugated antibodies can be purchased directly.

The device used for this assay will be the same as the one used in Example 1.

A mixture of 10 μl serum sample to be examined, 10 μl anti-AFP agarose beads, and 2.5 μl 20 nM HRP antiAFP antibody 320 will be incubated at room temperature for 30 minutes. Multiple assays with different samples and positive and negative controls can be performed simultaneously. 10 μl of each assay mixture can be added into the well of a device described in this invention. After the solution is absorbed, agarose beads will settle in the detection zone with a slurry volume of 2 μl. To rinse away the free HPR-antibodies, 50 μl rinsing buffer can be added into the well using a pipette for 4 times, 200 μl total. After all the rinsing buffer is absorbed, 10 μl HRP chemiluminescent substrate can be added onto the agarose beads. Different commercially available chemiluminescent substrate can be used, such as the Clarity Western ECL substrate from Bio-Rad, or Super-Signal West Femto Chemiluminescent Substrate from Thermo Scientific. Immediately after 10 minute incubation at room temperature, the plate can be inserted into a luminometer plate reader for signal detection. The plate reader should be configured into a top-reading mode, with appropriate setting for luminescence detection. The chemiluminescent signal can also be detected and imaged in a gel imaging system. The concentration of AFP in the sample can be obtained by referring to a calibration curve obtained under the same assay condition using AFP standards.

Example 3

Botulinum Neurotoxin Type A (BoNT/A) Fluorescence Resonance Energy Transfer (FRET) Assay This example shows how the device in this invention can be used to rapidly detect active BoNT/A in a large volume of serum sample using polyacrylamide beads and a FRET substrate (see FIG. 8).

The assay will need to use the following reagents: (1) Polyacrylamide beads 400 functionalized with anti-BoNT/A antibody 410; (2) serum sample that may contain the active BoNT/A molecule 420; (3) assay buffer 20 mM HEPES at pH 8.0; and (4) SNAPtide fluorogenic BoNT/A substrate 430 from EMD Millipore.

BoNT/A antibody (Santa Cruz Biotechnology) can be crosslinked to pre-activated polyacrylamide (PA) beads such as Ultralink Biosupport from Thermo Scientific. The anti-BoNT/A PA beads can be stored at 20% slurry in PBS solution containing 1% BSA with 0.5% Tween-20. 10 μl anti-BoNT/A PA beads will be added into 500 μl serum sample and incubated at 37° C. for 1 hour with slow rotation. The mixture will be added into a device described in this invention. For this assay, the device will have well which is 7 mm in diameter, 5 mm in height, a detection zone which is 2 mm in diameter and 1 mm in height, 7 mm diameter and 0.5 mm thick glassfiber membrane disc with 2.7 micrometer pore size, and an 8 mm×8 mm×20 mm porous polyethylene absorbing plug with 60-70% pore volume. Devices assembled in 8-well strip format with inter-device distance of 9 mm are inserted into a 96 well strip frame.

Multiple assays can be performed simultaneously. After the 500 μl sample solution is totally absorbed, the PA beads with captured BoNT/A target collected in the detection zone can be rinsed with 200 μl assay buffer. Finally, 10 μl SNAPtide substrate at appropriate working concentration, typically between $5\text{-}10\times10^{-6}$ M, will be added onto the beads. The plate can be placed inside a 37° C. humidified incubator for 10 minute for the reaction, after which the FRET signal will be measured from the plate. If active BoNT/A is present on the beads, the FRET substrate will be cleaved and the fluorophore will be released. Fluorescent intensity measured with excitation wavelength at 320 nm and emission wavelength at 420 nm will indicate the concentration of active BoNT/A in the sample with reference to a standard curve.

Example 4

Human Interleukin-6 (IL6) Fluorescence Immunoassay

This example shows how a device described in this invention was used to obtain a standard calibration curve for a rapid fluorescent immunoassay to detect target protein from human serum sample.

The device used for this assay will be the same as the one used in Example 1. The reagents used in this assay include the following: (1) Agarose beads functionalized with anti-human IL6 antibody (Agr-antiIL6); (2) Alexa Fluor 647-labeled anti-human IL6 antibody (AF647-antiIL6); (3) recombinant human IL6 as assay standard; and (4) 1% BSA-PBST as dilution buffer and rinsing buffer.

Agr-anti IL6 was prepared using glyoxal agaorse beads (Agarose Beads Technologies) and goat anti-IL6 polyclonal antibody (R&D Systems) according to manufacturer's instructions. They were stored in PBST-1% BSA buffer at 20% bead volume before use. AF647-anti IL6 was prepared with Alexa Fluor® 647 Antibody Labeling Kit (Life Technologies) and goat anti-IL6 polyclonal antibody (R&D Systems) according to manufacturer's instructions.

A 10-fold serial dilution of the human IL6 was prepared using the PBST-1% BSA dilution buffer. For each concentration of the IL6 standard, 10 μl IL6, 10 μl Agr-anti IL6, and 1 μl 100 nM AF647-anti IL6 were mixed together in a 1.5 ml centrifuge tube. Multiple reactions were started simultaneously. After 30 min incubation at room temperature, 20 μl of each reaction mix was added into the sample wells of the device. After the solution was absorbed, agarose beads settled in the detection zone. To rinse, 50 μl rinsing buffer was added into the well and this was repeated for 4 times. A total of 200 μl rinsing buffer was used and fully absorbed by the device. The plate was then inserted into a fluorescent microplate reader (TECAN) for signal detection. The plate was configured into a top-reading mode, with excitation wavelength at 652 nm and emission wavelength at 680 nm, and light beam focused at the detection zone.

The assay results with IL6 concentration ranging from 10 pg/ml to 100 ng/ml are displayed in FIG. 9. The fluorescent signal detected from the agarose beads increased as the concentration of IL6 increases. The standard curve can be used to find out the IL6 concentration in an unknown sample. The entire assay only took 30 min of incubation time and less than 10 min hands-on processing time, without using vacuum, magnet, centrifugation, etc., just pipetting solution into the device. The Fluorescent signal level was stable for at least 10 min.

Example 5

Mouse Immunoglobulin G (IgG) Chemiluminescent Dot Blot

This example shows how a device described in this invention was used for a rapid chemiluminescent dot blot assay to probe a mouse IgG dissolved in PBS.

This example use the same embodiment of the device as described in Example 1, except that the filter membrane is an untreated glassfiber filter membrane with 0.7 μm pore size.

Figure 10A:
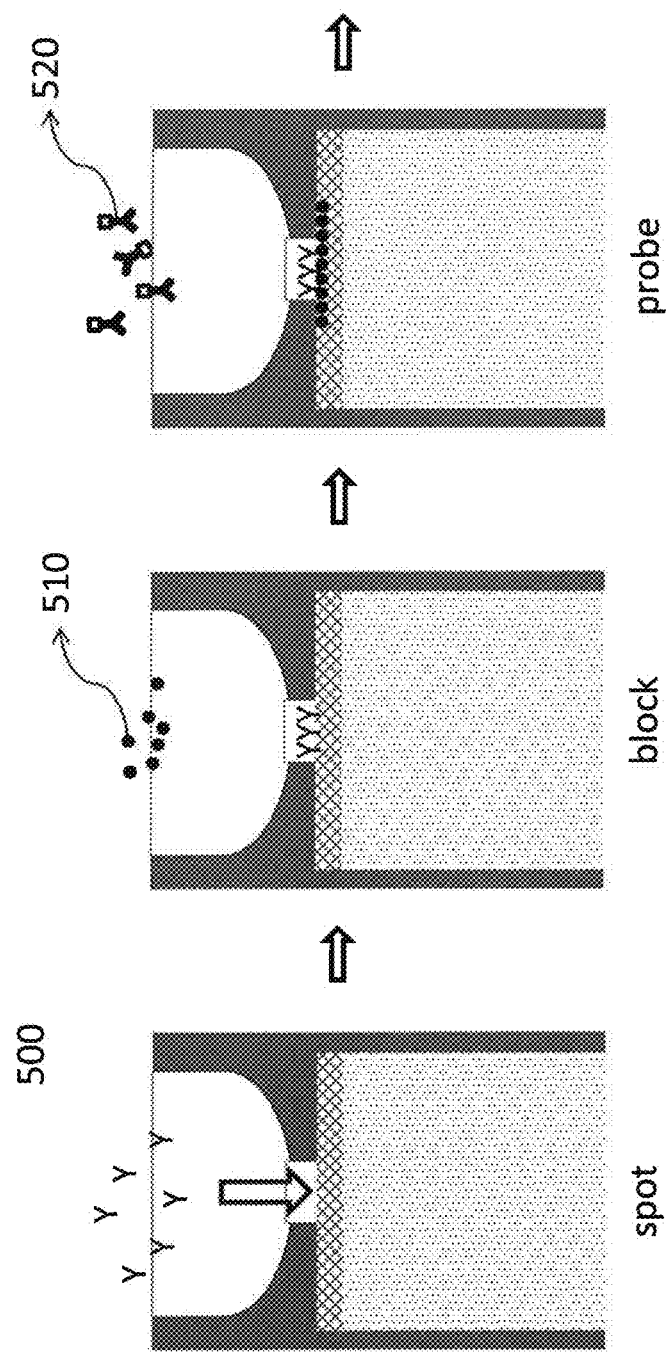
FIGS. 10A and 10B are schematic illustrations of the process of a chemiluminescent dot blot assay using the apparatus as described in the present disclosure.
Figure 10B:
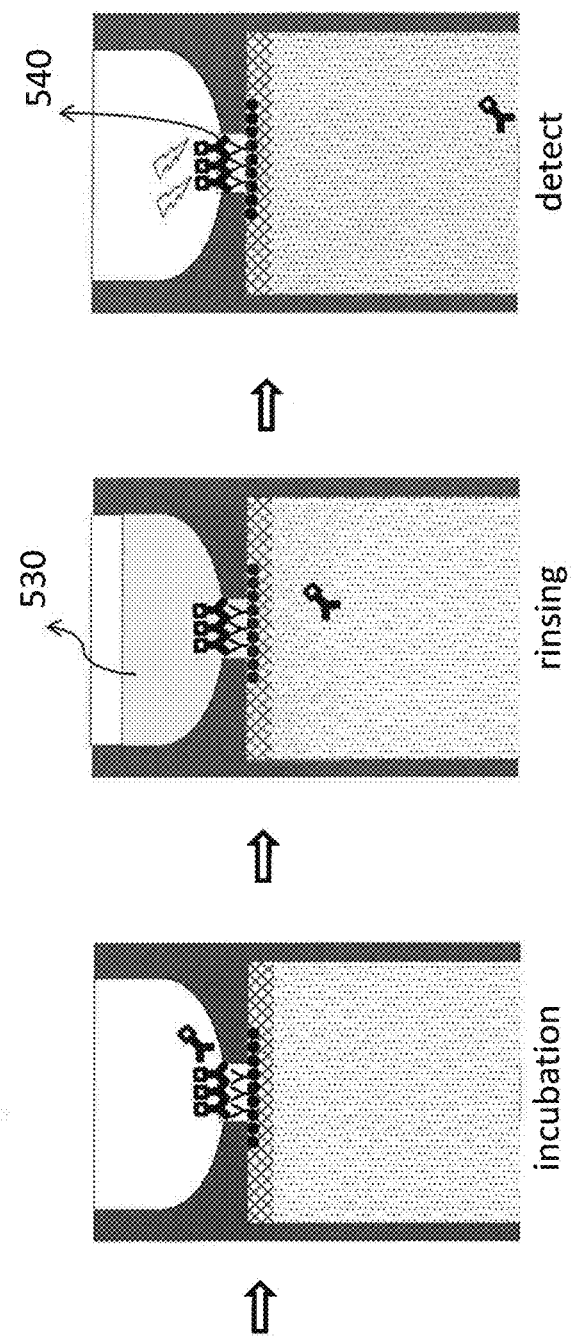

The assay process is illustrated in FIGS. 10A and 10B. Mouse IgG (R&D Systems) 500 was diluted in PBS to make 100 ng/ml, 10 ng/ml and 1 ng/ml samples. 1 μl of each sample was directly spotted onto the center of the untreated glassfiber membrane inside the well. The membrane was let dry in air for 20 min. 50 μl of 10% BSA 510 was added into each well and let sit for 15 min for blocking. For probing, 1 μl of 5 nM goat anti-mouse IgG conjugated with horse radish peroxidase (goat anti-mouse IgG-HRP) (KPL) 520 was added onto the membrane and let incubate for 5 min. To rinse, 50 μl of PBST-1% BSA 530 was added into the well and let absorbed completely. This step was repeated for 4 times. Immediately after 10 μl of chemiluminescent HRP substrate 540, SuperSignal Femto® (Thermo Scientific), was added into each well, the device was placed inside a digital gel imaging system (ProteinSimple) for a chemiluminescent (CL) image obtained with 1 second exposure time.

Figure 11:
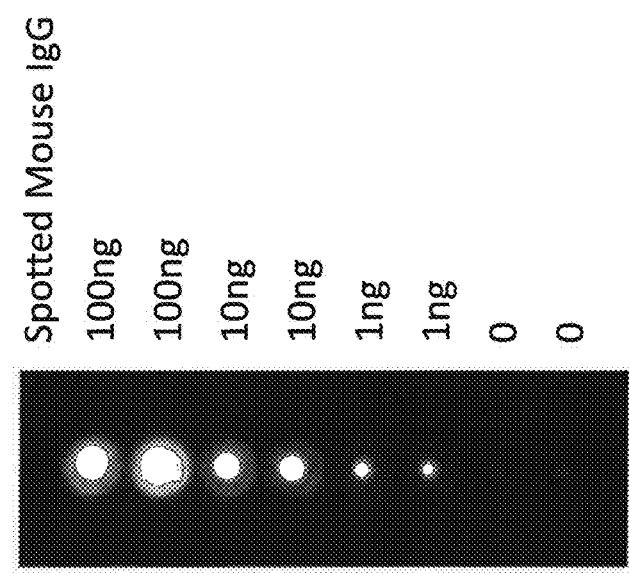
FIG. 11 is a chemiluminescent image resulting from a dot blot assay using the apparatus as described in the present disclosure.

The resulting CL image is shown in FIG. 11. For increasing amount of mouse IgG spotted onto the membrane, there are stronger CL signal from the sample well. The sensitivity of the assay is comparable to a conventional dot blot. The entire process took less than an hour, much less than hours or overnight procedure using conventional methods.

What is claimed is:

1. A device for biomolecule analysis, said device comprising: a filter membrane having an upper surface and a lower surface a sample well comprising a top opening for sample addition and a bottom opening, wherein the bottom opening of said sample well is disposed on the upper surface of said filter membrane and defines a detection zone, wherein the cross section of the detection zone has a circular shape, and a diameter from about 0.5 mm to 7 mm and a height from about 0.2 mm to about 2 mm; a porous absorbing plug having a surface, wherein the surface of the absorbing plug is in contact with the filter membrane and wherein the absorbing plug is a hydrophilic porous material having from about 30 to about 90 percent pore volume, with liquid absorbing capacity from about 10 μl to about 50 ml; and a housing, wherein the filter membrane, the sample well and the absorbing plug are disposed in said housing.

2. The device of claim 1, wherein the absorbing plug has a bottom surface, which is in contact with a hydrophobic membrane.

3. The device of claim 1, wherein the sample well has a sloped inner surface around the bottom opening, and wherein the volume of the sample well is from about 20 μl to about 10 ml.

4. The device of claim 1, wherein the cross-section of the sample well has a shape selected from the group consisting of circle, oval, square, rectangle, pentagon, hexagon and octagon, with sharp or rounded corner, or a combination thereof.

5. The device of claim 1, wherein the sample well is made of a material selecting from the group consisting of polypropylene, poly(methyl methacrylate) (PMMA), polystyrene, acrylonitrile butadiene styrene (ABS), polycarbonate (PC), nylon or combinations thereof.

6. The device of claim 1, wherein the filter membrane is a hydrophilic porous membrane having a plurality of void spaces or pores, wherein the plurality of void spaces has a dimension ranging from about 0.2 μm to about 50 μm.

7. The device of claim 1, wherein the filter membrane is selected from the group consisting of a silver membrane, a glassfiber filter membrane, a nitrocellulose membrane, a mixed cellulose ester (MCE) membrane, a polycarbonate (PC) membrane, a polyester (PE) membrane, a cellulose acetate membrane, a nylon membrane, a polyethersulfone (PES) membrane, a polyvinylidene difluoride (PVDF) membrane, a regenerated cellulose (RC) membrane, porous polyethylene (PE) membrane and porous polypropylene (PP) membrane.

8. The device of claim 1, wherein the filter membrane is a borosilicate glassfiber filter membrane having a plurality of pores, wherein the plurality of pores has a pore size ranging from about 0.3 μm to about 5.0 μm.

9. The device of claim 1, wherein the filter membrane is a nitrocellulose or mixed cellulose ester (MCE) filter membrane having a plurality of pores, wherein the plurality of pores has a pore size ranging from about 0.2 μm to about 5 μm.

10. The device of claim 1, wherein the filter membrane is a nylon membrane having a plurality of pores, wherein the plurality of pores has a pore size ranging from about 0.45 μm to about 5 μm.

11. The device of claim 1, wherein the filter membrane is a porous membrane treated with one or more blocking agents, wherein the blocking agents bind to the surface of the membrane through adsorption or chemical cross-linking.

12. The device of claim 1, wherein the absorbing plug is in contact the lower surface of the filter membrane.

13. The device of claim 1, wherein the absorbing plug is in contact with the upper surface of the filter membrane and wherein the portion of the filter membrane in contact with the absorbing plug is located outside the sample well.

14. The device of claim 1, wherein the cross section of the absorbing plug has a shape selected from the group consisting of circle, oval, square, rectangle, pentagon, hexagon and octagon, each of which has a sharp or rounded corner or a combination thereof.

15. The device of claim 12, wherein the absorbing plug comprises one or more voids situated beneath the bottom opening of the sample well, with a cross-section dimension equal or greater than that of the bottom opening of the sample well, and a height from about 0.5 mm to the height of the absorbing plug under the membrane.

16. The device of claim 1, wherein the absorbing plug is made of one or more hydrophilic porous materials selected from the group consisting of glassfiber, cellulose acetate fibers, cotton, porous polyethylene (PE), and polyethylene (PE)/polyester (PET) sheath/core fiber.

17. The device of claim 1, wherein a portion of the absorbing plug is made of hydrophilic polyethylene (PE)/polyester (PET) sheath/core bonded fiber, with the fiber aligned in a direction perpendicular to the surface of the filter membrane.

18. The device of claim 1, wherein the housing, sample well, filter membrane and absorbing plug are placed together in contact through injection molding, friction, or a bonding method selected from welding or adhesion.

19. The device of claim 1, wherein the housing and the sample well are molded into one piece.

20. The device of claim 1, wherein the filler membrane and absorbing plug are blended into a single component.

21. A plate for biomolecule analysis comprising a rectangular array of fixed or removable devices, each of the devices comprising: a filter membrane having an upper surface and a lower surface; a sample well comprising a top opening for adding sample and a bottom opening, wherein the bottom opening of said sample well is disposed on the upper surface of said filter membrane and defines a detection zone, wherein the cross section of the detection zone has a circular shape, and a diameter from about 0.5 mm to about 7 mm and a height from about 0.2 mm to about 2 mm; a porous absorbing plug having a surface, wherein the surface of the absorbing plug is in contact with the filter membrane and wherein the absorbing plug is a hydrophilic porous material having from about 30 to about 90 percent pore volume, with liquid absorbing capacity from about 10 μl to about 50 ml; and a housing, wherein the filter membrane, the sample well and the absorbing plug are disposed in said housing.

22. The plate of claim 21, having a width of about 127.8 mm, length of about 85.5 mm, and height ranging from about 14 mm to about 30 mm.

23. The plate of claim 21, wherein the distance between two adjacent devices is from about 3 mm to about 30 mm.

24. The plate of claim 21, wherein the plate comprises the array of devices arranged in a rectangular format selected from the group consisting of 1×1, 8×1, 8×2, 1×12, 2×12, 8×12, 6×1, 1×8, 6×8, 4×1, 1×6, 4×6, and 16×24 format.

25. The plate of claim 23, wherein the plate comprises devices arranged in a rectangular 1×1, 8×1, 8×2, 1×12, 2×12, or 8×12 format, wherein the distance between two adjacent devices is about 9 mm.

26. The plate of claim 23, wherein the plate comprises devices arranged in a rectangular 1×1, 6×1, 1×8, or 6×8 format, wherein the distance between the adjacent devices is about 12 mm.

27. The plate of claim 23, wherein the plate comprises devices arranged in a rectangular 1×1, 4×1, 1×6, and 4×6 format, wherein the distance between the adjacent devices is about 18 mm.

28. The plate of claim 23, wherein the plate comprises devices arranged in a rectangular 16×24 format, wherein the distance between the adjacent devices is about 4.5 mm.

* * * * *